(12) United States Patent
Frerot et al.

(10) Patent No.: US 6,359,168 B1
(45) Date of Patent: Mar. 19, 2002

(54) COMPOUNDS DERIVED FROM MENTHOL AND USE AS REFRESHING AGENT

(75) Inventors: Eric Frerot, Ville-la-Grand (FR); Nicole Van Beem, Dully (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 09/576,991

(22) Filed: May 24, 2000

Related U.S. Application Data

(63) Continuation of application No. PCT/IB98/01821, filed on Nov. 16, 1998.

(51) Int. Cl.$^7$ .............................. C07C 69/66; A23L 1/22
(52) U.S. Cl. ...................................... 560/186; 426/534
(58) Field of Search ......................... 560/186; 426/533, 426/534

(56) References Cited

U.S. PATENT DOCUMENTS

| | | | |
|---|---|---|---|
| 4,766,153 A | * | 8/1988 | Casciani et al. |
| 5,266,592 A | * | 11/1993 | Grub et al. |
| 5,703,123 A | * | 12/1997 | Pelzer et al. |

FOREIGN PATENT DOCUMENTS

| | | |
|---|---|---|
| DE | 191547 | 1/1906 |
| DE | 26 08 226 | 2/1976 |
| EP | 0 507 190 | 10/1992 |
| EP | 0 583 651 | 2/1994 |

OTHER PUBLICATIONS

M.H. Palmer et al., Partial Asymmetric Synthesis of β–Hydroxy–acids. Part 1 β–Hydroxy–β–phenylbutyric Acid. Journal of the Chemical Society, pp. 931–938 (1960) {Abstract XP002091888}.

J.A. Reid et al., Partial Asymmetric Synthesis in a Reformatsky Reaction. Journal of the Chemical Society, pp. 3365–3368 (1949) {Abstract XP002091889}.

\* cited by examiner

*Primary Examiner*—Gary Geist
*Assistant Examiner*—Paul A. Zucker
(74) *Attorney, Agent, or Firm*—Winston & Strawn

(57) ABSTRACT

Compounds of formula (I)

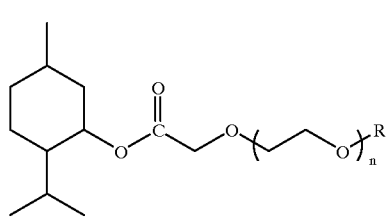

in which R=H or $CH_3$ and n is a whole number from 1 to 4. These compounds are useful as refreshing agents in various compositions, articles or products from flavor manufacture or perfumery.

13 Claims, No Drawings

COMPOUNDS DERIVED FROM MENTHOL AND USE AS REFRESHING AGENT

This application is a continuation of PCT/IB98/01821 filed Nov. 16, 1998.

TECHNICAL FIELD

The present invention relates to new compounds which have a cooling effect on the skin or mucous membranes, notably the buccal mucosae. More particularly, the application deals with compounds of the formula

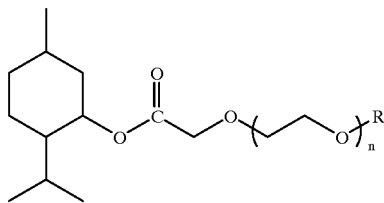

(I)

in which R=H and n is a whole number from 1 to 4 or R=$CH_3$ and n is a whole number from 0 to 4, as well as the use of the said compounds as cooling agents.

PRIOR ART

The prior art describes a large number of compounds of natural or synthetic origin, which have been observed to have a cooling effect on human skin or mucosae, the most well-known compound being (−)-menthol, which is found naturally in oil of mint, notably of mentha arvensis L and mentha viridis L.

Among the large number of publications in the field of synthetic cooling agents, particularly those derived from menthol, we should cite application DE-OS-2608226, which describes certain esters of menthol with hydroxylated carboxylic acids, for example glycolic acid, β-hydroxybutyric acid or α-hydroxycaprylic acid, but in particular the ester of lactic acid. Application EP-A-507190 describes cooling agents which are acetals of certain ketones, in particular 1-menthone glycerol ketal.

Application EP-A-583651 discloses another group of cooling agents derived from menthol, that is, asymmetric menthol carbonates, carbamates and thiocarbamates, in particular menthol ethylene glycol carbonate and menthol propane-1,2-diol carbonate.

In order to be suitable as a cooling agent, a compound must fulfill certain requirements. Firstly, the compound must not have an irritant effect on the skin or in particular the mucosae, which would prevent its use in certain applications, for example those in which the said compound is used in large quantities and/or the application product may come into contact with certain sensitive parts of the mucosae. For the reasons given above, the use of menthol is limited, as is the case also of other compounds which prove unsuitable for use in certain products.

Furthermore, for many applications it is desirable that the cooling effect be of prolonged duration, in order that this effect can still be perceived several minutes after the active agent is no longer in contact with the skin or mucosae. As menthol is highly volatile, it does not fulfill this condition in spite of its pronounced cooling effect.

In the majority of applications it is also desirable to have cooling agents which do not have a strong odour, as is the case of menthol which has the typical and pronounced odour of peppermint.

Finally, a cooling agent must not have an unpleasant taste, so that applications in the flavourings industry are possible. Once again, menthol has a marked bitter taste when used in high concentrations.

To summarise, it may be said that although menthol in particular, but also the other above-mentioned compounds which have a cooling effect, fulfill some of the above-mentioned conditions required of cooling substances ("cooling agents"), scientists are still searching for new compounds with properties which enable novel and preferably advantageous effects to be obtained in this field.

DESCRIPTION OF THE INVENTION

We have now synthesised a new class of compounds of general formula:

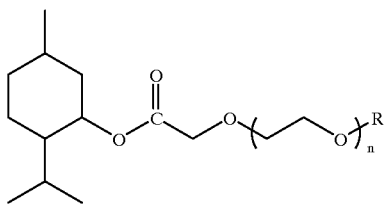

(I)

in which R=H and n is a whole number from 1 to 4, or R=$CH_3$ and n is a whole number from 0 to 4.

We have been able to establish that this class of compounds has all the desirable properties of a cooling agent, i.e.:

they are non-irritant compounds the cooling effect is pronounced and long-lasting the compounds do not have a strong odour the taste of the compounds is neutral, thus being able to reinforce the typical taste of the ingredients in flavour applications.

The class of compounds of formula (I) does not have the typical taste of menthol, but a more neutral taste which can vary according to the length of the chain linked to the carboxylic function, the nature of the terminal substituent on the said chain (H or $CH_3$), or the isomeric configuration of the menthol used as the starting substance for the preparation of the formula (I) compounds. In fact, the stereoisomery of compounds (I) is dictated by that of the starting menthol, and one can thus obtain all the stereoisomers of the compounds (I) corresponding to those of menthol. Of these stereoisomers, the formula (I) compounds derived from (−)-menthol are especially advantageous and preferred according to the invention for their marked cooling effect when used in the applications described below.

As formula (I) shows, the compounds according to the invention may have an alcohol or methoxy group in the terminal position of the chain. In the context of the present invention the use of compounds having a methoxy group in the terminal position is preferred.

Of the said compounds, the ones preferred are those which comply with formula (I) in which n=0 or 1, i.e. (−)-menthyl methoxyacetate, or (1R,2S,5R)-3-menthyl methoxyacetate, and (−)-menthyl 3,6-dioxaheptanoate, or (1R,2S,5R)-3-menthyl 3,6-dioxaheptanoate. (−)-Menthyl methoxyacetate has a head note fruity taste resembling that of menthyl acetate, whereas (−)-menthyl 3,6-dioxaheptanoate has a bitter taste. These two compounds are highly advantageous in flavours and one or the other or even both of these compounds may be used, depending on the envisaged application. For example, in applications in which a bitter taste is undesirable, (−)-menthyl methoxyacetate will be preferred, while (−)-menthyl 3,6-dioxaheptanoate will be used in cases where the bitter taste is an advantage, for example in citrus-based edible products.

In accordance with another embodiment of the invention, a mixture of (−)-menthyl methoxyacetate and (−)-menthyl 3,6-dioxaheptanoate is used. In these mixtures, the two constituents may be present in highly variable relative proportions depending on the desired effect. In fact, the use of these mixtures enables certain gustatory characteristics of one or the other of these two compounds to be suppressed when they are less advantageous in certain applications, while reinforcing the refreshing effect. We have established that this synergistic effect between the two compounds was best manifested with mixtures containing the two compounds in similar quantities by weight, that is about 50% of each by weight; these mixtures are therefore preferred according to the invention.

However, given that each of the compounds is a useful cooling ingredient in itself, it is clear that the invention also relates to mixtures of the two compounds in which the proportion of each is varied from 0 to 100% by weight of the mixture.

Moreover, these two compounds also lend themselves to applications other than in the flavour industry, for example in body-care or cosmetic products.

Thus the compounds of the invention may be used in all fields in which a cooling effect is to be imparted to the products in which they are incorporated. By way of example one may cite beverages such as fruit juices, soft drinks or cold tea, ice creams and sorbets, sweets, confectioneries, chewing gum, chewing tobacco, cigarettes, pharmaceutical preparations, dental-care products such as dentifrice gels and pastes, mouth washes, gargles, body and hair care products such as shampoos, shower or bath gels, body deodorants and antiperspirants, after-shave lotions and balms, shaving foams, perfumes, etc.

The proportions in which the compounds of the invention may be incorporated into the various products mentioned above vary within a wide range of values. These values depend on the nature of the article or product to which a cooling effect is to be imparted and on the effect required, as well as on the nature of the co-ingredients in a given composition when the compounds-of the invention are used in a mixture with flavouring or perfuming co-ingredients, solvents or adjuvants commonly used in the art.

By way of example one may cite typical concentrations of the order of 0.001 to 5% or even more, preferably 0.002 to 1%, by weight of this compound relative to the cooling finished product in which it is incorporated.

It should be noted that the concentrations of the compounds of the invention used in these applications depend both on the product to be flavoured and on the desired effect. Thus for example in applications such as beverages and sweets, concentrations of the order of 0.005 to 0.1% will typically be used, whereas for flavouring dentifrices and chewing gums the compounds of the invention will typically be used in concentrations within the range 0.2–0.3 and 0.5–1%.

The syntheses used to obtain the products of formula (I) all use menthol as the starting substance. One of the possible syntheses consists in an esterification of the said menthol with acetic acid which is substituted at position α, that is to say a compound of formula

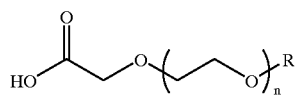

(II)

in which n and R have the meanings assigned in formula (I). The reaction takes place under the catalytic action of an acid, such as for example p-toluenesulphonic acid, phosphoric acid or any acid known for this type of esterification. The reaction is preferably performed in a solvent which permits separation of the water formed by azeotropic distillation, e.g. toluene, benzene or xylene.

Another synthesis involves, in the first stage, esterification of the menthol with α-halogenated acetic acid, preferably 2-bromoacetic acid. This esterification is performed under conditions similar to those described in the preceding paragraph. The menthyl 2-halogenoacetate thus obtained is then converted into the desired product by a "Williamson" etherification reaction. In this reaction, an alcoholate of a compound of formula

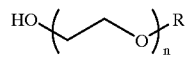

As the alcoholate one may use the alcoholate of an alkali metal, preferably sodium. An aprotic polar solvent such as, for example, dimethyl formamide, is preferably used for the Williamson reaction.

After the reaction, the formula (I) compounds are isolated and purified by conventional techniques, for example distillation or chromatography.

The invention will now be described in greater detail in the examples below, in which temperature is indicated in degrees Celsius and the abbreviations have the usual meaning in the art.

EXAMPLE 1

Preparation of (1R,2S,5R)-3-methyl methoxyacetate

A solution of (−)-menthol (50 g, 320 mmol), methoxyacetic acid (29 g, 320 mmol) and monohydrated p-toluenesulphonic acid (5 g, 26 mmol) is brought to reflux for 3 h in 500 ml of toluene. The water released during the reaction is separated by azeotropic distillation. The mixture is washed 3 times with 100 ml of a 5% NaOH solution, then twice with 100 ml of brine, the organic solvent is dried on $Na_2SO_4$ and the solvent evaporated under vacuum. Distillation is then performed under vacuum to recover 51 g (81%) of a colourless liquid (boiling point 75° C./3 Pa) with a purity≧99%.

MS(EI): 83(100), 45(52), 55(48), 69(36), 139(28), 41(26), 97(19), 95(18),29(14), 123(6), 155(1), 185(1), 213 (1)

$^1$H-NMR (400 MHz, $CDCl_3$): 4.81(dt, J=11.0, 4.4 Hz, 1H)); 4.04, 3.98 (AB, 2H); 3.45 (s, 3H); 2.02, 1.99 (2m, 1H); 1.82 (m, 1H); 1.71, 1.68 (2m, 2H); 1.50 (m, 1H); 1.40 (m, 1H); 1.14–0.82 (series of multiplets, 3H); 0.91 (d, J=5.6 Hz, 3H); 0.89 (d, J=6.8 Hz, 3H); 0.77 (d, J=6.8 Hz, 3H) δ ppm $^{13}$C-NMR(90 MHz, $CDCl_3$): 169.8 (s); 74.8 (d), 70.0 (t), 59.3 (q), 47.0 (d); 40.9 (t); 34.2 (t); 31.4(d); 26.3 (d): 23.4 (t); 22.0(q); 20.7 (q); 16.3 (q) δ ppm

EXAMPLE 2

Preparation of (1R,2S,5R)-3-menthyl 3,6-dioxaheptanoate

A solution of (−)-menthol (5 g, 32 mmol), (2-methoxyethoxy)acetic acid (4.3 g, 32 mmol) and monohydrated p-toluenesulphonic acid (0.5 g, 2.63 mmol) is brought to reflux for 3 h in 50 ml toluene. The water generated during the reaction is separated by azeotropic distillation. 150 ml toluene is added and the mixture is washed 3 times with 50 ml of a 5% NaOH solution, then twice with 50 ml of brine, the organic solvent is dried on $Na_2SO_4$ and the solvent evaporated under vacuum. Distillation under vacuum is then performed to recover 6.47 g (74%) of a colourless liquid (boiling point 110° C./3 Pa) with a purity of 98%.

MS(EI): 83(100), 55(45), 59(38), 69(36), 138(28), 45(23), 97(19), 29(16), 123(6), 109(3), 192(2), 155(1)

$^1$H-NMR (400 MHz, $CDCl_3$): 4.78 (dt, J=10.4, 4.4 Hz, 1H); 4.16, 4.08 (AB, 2H); 3.72 3.50 (2m, 4H); 3.40 (s, 3H); 2.02, 1.99 (2m, 1H); 1.82 (m, 1H); 1.71, 1.68 (2m, 2H); 1.50 (m, 1H); 1.39 (m, 1H); 1.14–0.82 (series of multiplets, 3H); 0.92 (d, J=6.3 Hz, 3H); 0.89 (d, J=6.8 Hz, 3H); 0.77 (d, J=6.8 Hz, 3H) δ ppm $^{13}$C-NMR(90 MHz, $CDCl_3$): 170.0 (s); 74.8 (d), 71.9 (t), 70.7 (t), 68.8 (t); 59.0 (q); 47.0 (d); 40.9 (t); 34.2(t): 31.4 (d); 26.3 (d); 23.4(t); 22.0 (q); 20.7 (q); 16.3 (q) δ ppm

EXAMPLE 3

Preparation of (1R,2S,5R)-3-menthyl 3,6,9-trioxadecanoate

A solution of (−)-menthol (5 g, 32 mmol), [2-(2-methoxyethoxy)ethoxy]acetic acid (5.7 g, 32 mmol) and monohydrated p-toluenesulphonic acid (0.6 g, 3.2 mmol) is brought to reflux for 3 h in 20 ml toluene. The water given off during the reaction is separated by azeotropic distillation. 150 ml toluene is added, the mixture is washed 3 times with 50 ml of a 5% NaOH solution, then twice with 50 ml of brine, the organic solvent is dried on $Na_2SO_4$ and the solvent evaporated under vacuum. Distillation is then performed under vacuum to recover 8.61 g (80%) of a colourless liquid (boiling point 160° C./1 Pa) with a purity of 96%.

MS(EI): 83(100), 59(74), 55(45), 103(44), 69(36), 138 (34), 45(34), 95(22), 29(22), 133(16), 147(10), 178(8), 284(1)

$^1$H-NMR (400 MHz, $CDCl_3$): 4.78(dt, J=10.4, 4.4 Hz, 1H)); 4.15, 4.09 (AB, 2H); 3.75 3.71, 3.66, 3.55 (4m, 4H); 3.38 (s, 3H); 2.02, 1.99 (2m, 1H); 1.82 (m, 1H); 1.71, 1.68 (2m, 2H); 1.50 (m, 1H); 1.39 (m, 1H); 1.13–0.82 (series of multiplets, 3H); 0.92 (d, J=6.3 Hz, 3H); 0.89 (d, J=6.8 Hz, 3H); 0.76 (d, J=6.8 Hz, 3H) δ ppm $^{13}$C-NMR(90 MHz, $CDCl_3$): 170.1 (s); 74.8 (d); 72.0, 70.9, 70.64, 70.58, 68.8 (5t); 59.1 (q); 47.0 (d); 40.9 (t); 34.2 (t); 31.4 (d); 26.3 (d); 23.5 (t); 22.0(q); 20.7 (q); 16.3 (q) δ ppm

EXAMPLE 4

Preparation of (1R,2S,5R)-3-menthyl 3.6,9-trioxadecanoate

This substance was synthesised in two stages:

a) For the first stage, a solution of (−)-menthol (1.56 g, 10 mmol), 2-bromoacetic acid (1.39 g, 10 mmol) and monohydrated p-toluenesulphonic acid (0.5 g, 2.6 mmol) was brought to reflux for 3 h in 100 ml toluene. The water given off during the reaction is separated by azeotropic distillation. 100 ml toluene is added, and the mixture is washed 3 times with 10 ml of a 5% NaOH solution, then twice with 100 ml of brine, the organic solvent is dried on $Na_2SO_4$ and the solvent evaporated under vacuum. The menthyl 2-bromoacetate obtained (2.45 g, 89%) is used in the next step without purification.

b) The second stage consists in what is known as a "Williamson" reaction.

The tetraethylene glycol monomethyl ether alcoholate (1.87 g, 9 mmol) is produced by heating the said alcohol with sodium (0.23 g, 10 mmol) in dimethyl formamide (20 ml) for 4 h at 60° C. The menthyl bromoacetate obtained earlier (2.45 g, 9 mmol) is then added and the mixture stirred for 3 h at 60–80° C. and then 16 h at ambient temperature. 200 ml ethyl acetate is added and the mixture is washed 3 times with 20 ml of a 5% $KHSO_4$ solution, then 3 times with a 5% NaOH solution, and then twice with 20 ml of brine. The organic solvent is dried on $Na_2SO_4$ and the solvent evaporated under vacuum. The product is purified by flash chromatography on silica gel eluted with a mixture of cyclohexane/ethyl acetate (60/40). 0.5 g of a slightly yellow oil (14%) is obtained. The reaction has not been optimised.

MS(CI, $NH_3$): 422(100, $M^+NH_4^+$), other fragments minimal $^1$H-NMR (400 MHz, $CDCl_3$): 4.78(dt, J=10.4, 4.4 Hz, 1H)); 4.15, 4.08 (AB, 2H); 3.72–3.50 (m series, 24H); 3.38 (s, 3H); 2.02, 1.99 (2m, 1H); 1.82 (m, 1H); 1.71, 1.68 (2m, 2H); 1.50 (m, 1H); 1.39 (m, 1H); 1.14–0.82 (series of multiplets, 3H); 0.92 (d, J=6.3 Hz, 3H); 0.89 (d, J=6.8 Hz, 3H); 0.77 (d, J=6.8 Hz, 3H) δ ppm $^{13}$C-NMR(90 MHz, $CDCl_3$): 170.1 (s); 74.8 (d); 72.0(t); series of triplets at 72.0 (t); 70.9(t), 70.6(t), 70.5(t) and 68.8 (t); 59.0 (q); 47.0 (d); 40.9 (t); 34.2 (t); 31.4 (d); 26.3 (d); 23.4 (t); 22.0 (q); 20.7 (q); 16.3 (q) δ ppm

EXAMPLE 5

Preparation of (1R,2S,5R)-3-menthyl (2-hydroxyethoxy)acetate

This substance was synthesised in three stages:

a) For the first step, NaH (60% in mineral oil, 1.97 g, 1.5 eq) is added in portions to a solution of 2-benzyloxyethanol (5 g, 32.85 mmol; source: Aldrich Chemicals) in 25 ml THF under argon. The resulting solution is brought to reflux for 1 h, then cooled to 25°.

A solution of sodium bromoacetate is prepared by adding NaH in portions (1.3 g, 1 eq) to a solution of bromoacetic acid (4.56 g, 32.85 mmol) in 25 ml THF.

This solution of bromoacetate is added dropwise to the prepared solution of benzyloxyethanolate anion, and the mixture is heated at reflux for 19 h. The reaction is stopped with 5% $KHSO_4$. 250 ml ethyl acetate is added and the organic phase is extracted three times with the aid of 5% NaOH. The pH of the alkaline phase is reduced to 1 with 10% HCl and extraction is performed twice with EtOAc. The organic phase is washed three times with sodium chloride solution, dried on $Na_2SO_4$, and evaporated to obtain 6.4 g (93%) 7-phenyl-3,6-dioxaheptanoic acid in the form of a colourless liquid.

b) A mixture of 7-phenyl-3,6-dioxaheptanoic acid (6.36 g, 30.3 mmol), (−)menthol (4.73 g, 1 eq) and p-toluenesulphonic acid (0.63 g, 0.11 eq.) is heated azeotropically at reflux for 3 h in 40 ml toluene. Ethyl acetate is added, and the organic phase is washed three times with the aid of 5% $NaHCO_3$, three times with brine, then dried on $NaSO_4$ and evaporated to obtain 10.9 g of a pale yellow oil which is distilled under vacuum to obtain 8.96 g (85%, b.p. 145–147°/10-2 mmHg) of a colourless oil corresponding to (1R,2S,5R)-menthyl 7-phenyl-3,6-dioxaheptanoate.

c) The (1R,2S,5R)-menthyl 7-phenyl-3,6-dioxaheptanoate (8.9 g, 25.5 mmol) is hydrolysed for 16 h in 50 ml THF with the aid of Pd on 10% wood charcoal (0.89 g) as the catalyst. Ethyl acetate is added, then the reaction mixture is filtered on a Celite® bed, washed three times with brine, dried on $Na_2SO_4$ and evaporated. Flash chromatography is performed on silica gel (cyclohexane/EtOAc; 80/20) to obtain (1R,3R,4S)-menthyl (2-hydroxyethoxy) acetate in the form of a pale yellow liquid (5.37 g; 89.8%). Purity: 99.2% by gas-phase chromatography (DBI column, 15 m, 70° for 0.5 min then 70–220° at 10°/min, RT=11.76 min).

MS(EI): 83(100), 81(86), 95(85), 71(64),138(51), 123 (50), 55(43), 41(24), 102(19), 109(16), 29(12), 155(2)

$^1$H-NMR ($CDCl_3$): 4.81 (dt, J=10.7, 4.4 Hz, 1H); 4.16–4.09 (AB, J=16.7 Hz, 2H); 3.76 (m, 2H); 3.69 (m, 2H); 3.06 (s broad, 1H, OH exchangeable); 2.03–2.00 (2m, 1H); 1.83 (m, 1H); 1.72–1.68 (2m, 2H); 1.52 (m, 1H); 1.44–1.37 (m, 1H); 1.09–0.83 (m,3H); 0.93; 0.91 (2d, J=6.8 Hz, 6H); 0.78 (d, J=7.1 Hz, 3H) δ ppm $^{13}$C-NMR($CDCl_3$): 170.8 (s); 75.4 (d); 73.6 (t); 68.5 (t); 61.5 (t); 47.0 (d); 40.9 (t); 34.1 (t); 31.4 (d); 26.4 (d); 23.5 (t); 22.0 (q); 20.7 (q); 16.3 (q) δ ppm Taste: (1R,2S,5R)-menthyl (2-hydroxyethoxy)acetate is immediately and intensely cooling when tasted.

EXAMPLE 6

Preparation of (1R,2S,5R)-menthyl 11-hydroxy-3,6,9-trioxaundecanoate

This substance was synthesised in two stages:

a) For the first stage, (−)-menthol (20 g; 127 mmol) and 3,6,9-trioxaundecandioic acid (56.9 g; 2 eq; source: Fluka) is heated without solvent for 16 h at 120°, while drawing off the water continuously by distillation at 10 mmHg. The reaction mixture is diluted in ethyl acetate, washed 8 times with deionised water, dried on $Na_2SO_4$, and evaporated. Chromatography of the crude product is performed on silica gel (65/35 cyclohexane/ EtOAc with 1% acetic acid, then 40/60 with 1% ethanol) to obtain 25 g (1R,2S,5R)-menthyl hydrogeno-3,6,9-trioxaundecanedioate (54%) in the form of a colourless viscous liquid.

b) A borane tetrahydrofuran complex (1M, 20 ml) is added dropwise to a solution of (1R,2S,5R)-menthyl hydrogeno-3,6,9- trioxaundecanedioate (7.21 g; 20 mmol) in 72 ml THF at ambient temperature. The reaction is maintained with stirring for 4.5 h, then cooled to 0°. 5 ml NaOH is then added dropwise. The mixture is maintained with stirring for a further 10 min. Ethyl acetate is added, and the organic phase is washed 3 times with the aid of 5% $NaHCO_3$, three times with 5% $KHSO_4$, three times with brine, then dried on $Na_2SO_4$ and evaporated. Flash chromatography is performed on silica gel (cyclohexane/ EtOAc; 40/60) to obtain (1R,2S,5R)-menthyl 11-hydroxy-3,6,9-trioxaundecanoate in the form of a pale yellow liquid (2.22 g, 32%). Purity: 99.9% by gas-phase chromatography (DBI column, 15 m, 150° for 15 min, then 150–240° at 10°/min, RT=9.17 min).

MS(EI): 83(100), 45(52), 89(46), 138(45), 103(39), 69(31), 55(30) 147(15), 121 (15), 208(7), 163(6), 190(6), 177(5)

$^1$H-NMR ($CDCl_3$): 4.78 (dt, J=10.7, 4.4 Hz, 1H); 4.16; 4.09 (AB, J=16.7 Hz, 2H); 3.76–3.61 (m, 12H); 2.78 (s broad, 1H, OH exchangeable); 2.02; 1.98 (2m, 1H); 1.83 (m, 1H); 1.70; 1.66 (2m, 2H); 1.49 (m, 1H); 1.42–1.34 (m, 1H); 1.01–0.80 (m, 3H); 0.93; 0.91 (2d, J=5.9 Hz, 6H); 0.78 (d, J=6.7 Hz, 3H) δ ppm $^{13}$C-NMR($CDCl_3$): 170.1 (s); 75.0 (d); 72.7 (t); 70.7; 70.6; 70.5; 70.2 (4t); 68.7 (t); 61.6 (t); 47.0 (d); 40.9 (t); 34.2 (t); 31.4 (d); 26.3 (d); 23.4 (t); 22.0 (q); 20.7 (q); 16.3 (q) δ ppm Taste: (1R,2S,5R)-menthyl 11-hydroxy-3,6,9-trioxaundecanoate has a slightly bitter, mentholated taste. Its cooling effect develops more particularly on the tongue and in the throat.

EXAMPLE 7

Preparation of a dentifrice gel and a dentifrice paste (1R,2S,5R)-3-menthyl methoxyacetate and (1R,2S,5R)-3-menthyl 3,6-dioxaheptanoate were each added in a dosage of 0.4% to a dentifrice gel and a dentifrice paste of the conventional type, which had been prepared, for example, from the following ingredients:

Dentifrice gel

| Ingredients | % by weight |
| --- | --- |
| Sorbosil ® AC 77 [1] | 8 |
| Sorbosil ® AC 15 [1] | 9 |
| 70% Sorbitol | 66.642 |
| PEG 1500 | 2 |
| Sodium lauryl sulphate | 2.1 |
| Sodium monofluorophosphate | 0.76 |
| Sodium carboxymethylcellulose | 0.4 |
| Saccharin sodium salt | 0.2 |
| Blue colouring | 0.002 |
| Demineralised water | 0.896 |
| Total | 100.00 |

Dentifrice paste:

| Ingredients | % by weight |
| --- | --- |
| Sorbosil ® AC 77 [1] | 6.5 |
| Sorbosil ® AC 15 [1] | 9 |
| 70% Sorbitol | 40 |
| Sodium lauryl sulphate | 1.5 |
| Sodium monofluorophosphate | 0.8 |
| Sodium carboxymethylcellulose | 1.1 |
| Saccharin sodium salt | 0.2 |
| $TiO_2$ | 0.5 |
| Demineralised water | 40.4 |
| Total | 100.00 |

[1] A silica-based thickening agent; source: Crosfield Chemicals Ltd, Great Britain 1) A silica-based thickening agent; source: Crosfield Chemicals Ltd, Great Britain The products were then tested and evaluated by expert tasters under blind conditions. After use and rinsing of the mouth it was found that, in the case of both the products, a freshness which developed after rinsing lasted for 15 to 20 min. In a comparison with menthol, the substances of the invention cited above were judged to yield a freshness with a slow-release effect by comparison with that of menthol and, in addition, the typical taste of menthol was not perceived.

By introducing a mixture of the two previously mentioned compounds to the finished product in a dosage of 0.25% of each, a highly advantageous effect was obtained in this type of application by reducing both the fruitiness of (1R,3R,4S)-3-menthyl methoxyacetate and the bitterness of (1R,3R,4S)-3-menthyl-3,6-dioxaheptanoate by comparison with the products described above, which contained only one or the other of these compounds.

EXAMPLE 8

Preparation of Sweets

Grapefruit-flavoured sweets were prepared from boiled sugar, 1% citric acid, and 0.05% of a grapefruit flavouring of the following formula:

| Ingredients | Parts by weight |
| --- | --- |
| Styrallyl acetate | 25 |
| 0.1% Thiomenthone in ethanol | 30 |
| Grapefruit essence | 945 |
| Total | 1000 |

Under blind conditions, expert flavourists then compared these sweets, without any additives, with sweets of the same composition to which certain compounds according to the invention had been added.

In the opinion of the tasters, addition of 0.05% (1R,2S, 5R)-3-menthyl methoxyacetate yielded a freshness which does not modify the organoleptic profile of the base composition, that is, the sweets described above.

Addition of the same quantity of (1H,2S,5R)-3-menthyl-3,6-dioxaheptanoate yielded a similar freshness and, in addition, a bitterness which reinforced the natural bitterness of the grapefruit essence.

EXAMPLE 9

Preparation of Gelatin-based Confectioneries

By a method which is known per se, grapefruit-flavoured confectioneries were prepared from 30 g gelatin, 175 g water, 150 g sugar and 200 g glucose. We then added 0.8% citric acid and 0.08% of a grapefruit flavouring of the formula given in Example 6.

Under blind conditions, expert flavourists then compared this base preserve, without any additives, with preserve of the same composition to which certain compounds according to the invention had been added.

In the opinion of the tasters, addition of 0.05% of (1R, 2S,5R)-3-menthyl methoxyacetate by weight to the base preserve leaves a freshness in the mouth. Addition of 0.05% (1R,2S,5R)-3-menthyl 3,6-dioxaheptanoate has the same freshness effect, while also reinforcing the bitterness of the grapefruit flavouring.

EXAMPLE 10

Preparation of Lemon Sorbets

Lemon sorbets were prepared from the following ingredients using conventional techniques:

| Ingredients | % by weight |
| --- | --- |
| Sugar | 20 |
| Glucose syrup | 8 |
| Dextrose | 2.5 |
| Lemon juice concentrate | 1.5 |
| Meypyrogen IC 304 [1)] | 0.6 |
| Water | to 100% |
| Total | 100 |

1) A mixture of carob gum E410, guar gum E412, carrageenan E407, gelatin, emulsifier E471; source: Meyhall Chemical AG, Kreuzlingen, Switzerland 0.5% citric acid and 0.01% of lemon flavouring of the following formula were then added:

| Ingredients | Parts by weight |
| --- | --- |
| Citronellyl acetate | 2 |
| Geranyl acetate | 6 |
| Linalyl acetate | 2 |
| Citronellol | 2 |
| Geraniol | 3 |
| Terpineol | 5 |
| Citral | 5 |
| Lemon terpenes | 975 |
| Total | 1000 |

Under blind conditions, expert flavourists then compared this lemon sorbet, without any additives, with sorbets of the same composition to which certain compounds according to the invention had been added.

In the opinion of the tasters, addition of 0.05% by weight of (1R,2S,5R)-3-menthyl methoxyacetate to the above prepared base sorbet gave it a pleasant freshness in the mouth.

Addition of 0.003% (1H,2S,5R)-3-menthyl 3,6-dioxaheptanoate has a similar effect, but this compound also confers a bitterness which reinforces the "zesty" note of the lemon flavouring.

EXAMPLE 11

Preparation of Chewing Gum

Chewing gum was prepared from a Cafosa Navada Plus T 413-01chewing-gum base (18 parts by weight) (source: Cafosa Gum Products Technology, Barcelona, Spain), sugar (60 parts by weight), glucose (20 parts by weight) and glycerol (0.5 parts by weight). 0.8 parts by weight of citric acid and 1 part by weight of lemon flavouring according to the formula given in Example 8 were then added to this mixture. Under blind conditions, expert tasters then compared this chewing-gum base, without any additives, with chewing gums of the same composition to which certain compounds according to the invention had been added.

Thus the addition of 0.4 parts by weight respectively of (1R,3R,4S)-3-menthyl methoxyacetate or (1R,3R,4S)-3-menthyl 3,6-dioxaheptanoate to the chewing gum gives it a prolonged freshness, the fresh sensation occurring in the mouth after chewing.

EXAMPLE 12

Preparation of an Orange Drink

An orange-flavoured drink was prepared from a 65° Brix syrup which had been diluted to 10%, acidified with 1.5% citric acid and then flavoured with 0.01% of an orange flavouring of the following formula:

| Ingredients | Parts by weight |
| --- | --- |
| Hexanal | 3 |
| Octanal | 2 |
| Dodecanal | 3 |
| Ethyl butyrate | 15 |
| Acetic aldehyde | 30 |
| Orange essence | 947 |
| Total | 1000 |

Under blind conditions, expert tasters then compared this base drink, without any additives, with drinks of the same composition to which certain compounds according to the invention had been added.

In the opinion of the tasters, addition of 0.003% (1R,2S, 5R)-3-menthyl methoxyacetate give a sensation of freshness which develops as an after-taste.

Addition of 0.003% (1R,2S,5R)-3-menthyl 3,6-dioxaheptanoate has a similar effect, but this compound also confers a bitterness which reinforces the "zesty" note of the flavouring.

Comparative Example 1

Preparation of After-shave Lotions

Two after-shave lotions were prepared by a method which is known per se, starting with the following ingredients:

|   |    | Ingredients          | % by weight |
|---|----|----------------------|-------------|
| A | 1) | Cremophor ® RH-40 [1)] | 1.5         |
|   | 2) | 10% ethyl alcohol    | 98.0        |
|   | 3) | ML Frescolat ® [2)]  | 0.5         |

1) Hydrogenated and ethoxylated ricin oil; source: BASF AG, Ludwigshafen, Germany 2) (1R,2S,5R)-3-menthyl lactate; source: Haarmann & Reimer GmbH, Holzminden, Germany

|   |    | Ingredients                                  | % by weight |
|---|----|----------------------------------------------|-------------|
| B | 1) | Cremophor ® RH-40[1)]                        | 1.5         |
|   | 2) | 10% ethyl alcohol                            | 98.0        |
|   | 3) | (1R, 2S, 5R)-3-menthyl 3,6-dioxaheptanoate   | 0.5.        |

1) See lotion A

The two lotions thus obtained were poured into an aerosol-type bottle. They were then applied in a quantity of 300 mg to the forearm and cheek of each of the two people constituting the panel, and compared under blind conditions.

In the opinion of the panel, the lotion containing the compound according to the invention exhibited a cooling effect superior to that of the lotion containing the cooling agent of the prior art in 3 out of 4 tests conducted.

What is claimed is:
1. A compound of the formula

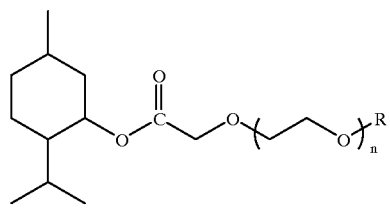

(I)

in which R=H or $CH_3$ and n is a whole number from 1 to 4.

2. The compound of claim 1, in the form of an isomer of configuration (1R,3R,4S).

3. The compound of claim 1 specifically as (1R,3R,4S)-3-menthyl-3,6-dioxaheptanoate.

4. The compound of claim 1 in the form of a mixture of (1R,3R,4S)-3-menthyl-3,6-dioxaheptanoate and (1R,3R,4S)-3-menthyl-methoxyacetate.

5. The mixture of claim 4 wherein each compound is present in a proportion of 50% by weight.

6. A flavoring composition or flavored product containing, as an ingredient, the compound of claim 1.

7. The flavored product of claim 6, in the form of a drink, an ice cream or sorbet, a sweet, a preserve, a chewing gum, a cigarette, chewing tobacco, a pharmaceutical preparation, a dental care product, or a body-care product.

8. The flavored product of claim 7, wherein the drink is a fruit juice, a soft drink or a tea.

9. The flavored product of claim 7, wherein the dental care product is a dentifrice gel or paste, a mouth wash or a gargle.

10. A perfumed product or perfumed article containing, as an ingredient, the compound of claim 1.

11. The perfumed article of claim 10 in the form of a shampoo, a shower or bath gel, a body deodorant or antiperspirant, an after-shave lotion or balm, a shaving foam, a cosmetic product or a perfume.

12. A method of reinforcing the taste of a flavored composition which comprises adding to the composition a compound according to claim 1 in an amount effective to enhance, modify or reinforce the flavor of the composition.

13. A method of reinforcing the odor of a perfumed composition which comprises adding to the composition a compound according to claim 1 in an amount effective to enhance, modify or reinforce the odor of the composition.

* * * * *

UNITED STATES PATENT AND TRADEMARK OFFICE
CERTIFICATE OF CORRECTION

PATENT NO. : 6,359,168 B1
DATED : March 19, 2002
INVENTOR(S) : Frerot et al.

It is certified that error appears in the above-identified patent and that said Letters Patent is hereby corrected as shown below:

<u>Title page,</u>
Add the following section:

-- Foreign Application Priority Data
Nov. 27, 1997 (CH) 1997 2743/97 --.

<u>Column 4,</u>
Line 25, after the formula, insert: -- in which n and R have meanings assigned in formula (I), is reacted with the menthyl 2-halogenoacetate mentioned above. --.

<u>Column 5,</u>
Lines 55-56, change "Preparation of (1R,2S,5R)-3-menthyl 3.6,9-trioxadecanoate" to -- Preparation of (1R,2S,5R)-3-menthyl 3,6,9,12,15-pentaoxahexadecanoate --.

<u>Column 6,</u>
Lines 33-34, change "Preparation of (1R,2S,5R)-3-menthyl (2-hydroxyethoxy)acetate" to -- Preparation of (1R,2S,5R)-menthyl (2-hydroxyethoxy)acetate --.

<u>Column 8,</u>
Lines 63-65, change each occurrence of "(1R,3R,4S)" to -- 1R,2S,5R) --.

<u>Column 9,</u>
Line 23, change "(1H,2S,5R)" to -- (1R,2S,5R) --.

<u>Colurnn 10,</u>
Line 22, change "(1H,2S,5R)" to -- (1R,2S,5R) --.
Line 41, change each occurrence of "(IR,3R,4S)" to -- (1R,2S,5R) --.

UNITED STATES PATENT AND TRADEMARK OFFICE
CERTIFICATE OF CORRECTION

PATENT NO. : 6,359,168 B1
DATED : March 19, 2002
INVENTOR(S) : Frerot et al.

It is certified that error appears in the above-identified patent and that said Letters Patent is hereby corrected as shown below:

Column 12,
Line 16, "(1R,3R,4S)" to -- (1R,2S,5R) --.
Line 17, "(1R,3R,4S)" to -- (1R,2S,5R) --.
Lines 20-21, change each occurrence of "(1R,3R,4S)" to -- (1R,2S,5R) --.

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,359,168 B1
DATED : March 19, 2002
INVENTOR(S) : Frerot et al.

It is certified that error appears in the above-identified patent and that said Letters Patent is hereby corrected as shown below:

<u>Title page,</u>
Add the following section:

-- Foreign Application Priority Data
Nov. 27, 1997 (CH) 1997 2743/97 --.

<u>Column 4,</u>
Line 25, after the formula, insert: -- in which n and R have meanings assigned in formula (I), is reacted with the menthyl 2-halogenoacetate mentioned above. --.

<u>Column 5,</u>
Lines 55-56, change "Preparation of (1R,2S,5R)-3-menthyl 3.6,9-trioxadecanoate" to -- Preparation of (1R,2S,5R)-3-menthyl 3,6,9,12,15-pentaoxahexadecanoate --.

<u>Column 6,</u>
Lines 33-34, change "Preparation of (1R,2S,5R)-3-menthyl (2-hydroxyethoxy)acetate" to -- Preparation of (1R,2S,5R)-menthyl (2-hydroxyethoxy)acetate --.

<u>Column 8,</u>
Lines 63-65, change each occurrence of "(1R,3R,4S)" to -- (1R,2S,5R) --.

<u>Column 9,</u>
Line 23, change "(1H,2S,5R)" to -- (1R,2S,5R) --.

<u>Column 10,</u>
Line 22, change "(1H,2S,5R)" to -- (1R,2S,5R) --.
Line 41, change each occurrence of "(1R,3R,4S)" to -- (1R,2S,5R) --.

UNITED STATES PATENT AND TRADEMARK OFFICE
CERTIFICATE OF CORRECTION

PATENT NO.    : 6,359,168 B1
DATED         : March 19, 2002
INVENTOR(S)   : Frerot et al.

It is certified that error appears in the above-identified patent and that said Letters Patent is hereby corrected as shown below:

Column 12,
Line 16, "(1R,3R,4S)" to -- (1R,2S,5R) --.
Line 17, "(1R,3R,4S)" to -- (1R,2S,5R) --.
Lines 20-21, change each occurrence of "(1R,3R,4S)" to -- (1R,2S,5R) --.

This certificate supersedes Certificate of Correction issued April 1, 2003.

Signed and Sealed this

Twenty-seventh Day of May, 2003

JAMES E. ROGAN
*Director of the United States Patent and Trademark Office*